US006979664B1

(12) United States Patent
Smith et al.

(10) Patent No.: US 6,979,664 B1
(45) Date of Patent: Dec. 27, 2005

(54) COMPOSITION FOR ACCELERATING SEED GERMINATION AND PLANT GROWTH

(75) Inventors: Donald Smith, Sainte-Anne-de-Bellevue (CA); Pan Bo, Sainte-Anne-de-Bellevue (CA); Yinghai Deng, Montreal (CA); Pierre Migner, Saint-Anne-de-Bellevue (CA); Feng Zhang, Sainte-Anne-de-Bellevue (CA); Balakrishnan Prithiviraj, Sainte-Anne-de-Bellevue (CA); Ahsan Habib, Sainte-Anne-de-Bellevue (CA)

(73) Assignees: Bios Agriculture Inc., Ontario (CA); McGill University, Quebec (CA)

( * ) Notice: Subject to any disclaimer, the term of this patent is extended or adjusted under 35 U.S.C. 154(b) by 0 days.

(21) Appl. No.: 09/744,129

(22) PCT Filed: Jul. 21, 1999

(86) PCT No.: PCT/CA99/00666

§ 371 (c)(1), (2), (4) Date: Jun. 21, 2001

(87) PCT Pub. No.: WO00/04778

PCT Pub. Date: Feb. 3, 2000

(30) Foreign Application Priority Data

Jul. 21, 1998 (CA) .................................... 2243669

(51) Int. Cl.[7] .................. A01N 43/16; A01N 63/00
(52) U.S. Cl. ...................................... 504/117; 504/292
(58) Field of Search ....................... 504/117, 113, 313, 504/292

(56) References Cited

U.S. PATENT DOCUMENTS

| | | | |
|---|---|---|---|
| 5,175,149 A | * | 12/1992 | Stacey et al. ................ 514/23 |
| 5,321,011 A | | 6/1994 | Stacey et al. |
| 5,545,718 A | | 8/1996 | Plaue et al. |
| 5,549,718 A | | 8/1996 | Lerouge et al. |

FOREIGN PATENT DOCUMENTS

| | | |
|---|---|---|
| CA | 2179879 | 12/1997 |
| GB | 2 080 669 | 2/1982 |
| WO | WO 91/15496 | 10/1991 |
| WO | WO 94/00466 | 1/1994 |
| WO | WO 97/26363 | 7/1997 |

OTHER PUBLICATIONS

Rohrig et al., Growth of Tobacco Protoplasts Stimulated by LCO, 1995, Science vol. 269 pp. 841-843.*

(Continued)

*Primary Examiner*—S. Mark Clardy
(74) *Attorney, Agent, or Firm*—Merchant & Gould P.C.

(57) ABSTRACT

Lipo Chitooligosaccharide (LCO) [NodBj-V(C18:1,Me-fuc)] isolated from *Bradyrhizobium japonicum* strain 532C was able to stimulate seed germination/seedling emergence, or in the case of potato, sprouting, of a number of crop plants representing eight distantly related plant families (Poaceae, Fabaceae, Brassicaceae, Cucurbitaceac, Malvaceae, Asteraceae, Chenopodiaceae and Solanaceae) of plants, at 25 and/or at 15° C. It also promoted sprouting potato minitubers. Other LCOs [NodRM-V($C_{16:2,5}$) and LCO from *R. leguminosarum*] were also shown to also display growth-promoting effects on the tested crop plants. The compositions comprising at least one LCO are shown to be effective in promoting growth under both laboratory and field conditions. The invention thus also relates to methods for promoting seed germination and/or seedling emergence and/or growth of plants comprising subjecting the seeds and/or plants to an effective amount of an agricultural composition comprising at least one LCO.

35 Claims, 1 Drawing Sheet

OTHER PUBLICATIONS

Spaink, Herman P. "Regulation of Plant Morphogenesis by Lipo-Chitin Oligosaccharides". Critical Reviews in Plant Sciences. 15(5&6):559-582. 1996.*

Stokkemans et al. . "Structural Requirements of Synthetic and Natural Product Lipo-Chitin Oligosaccharides for Induction of Nodule Primordia on Glycine soja". Plant Physiology. 108:1587-1595. 1995.*

Schlaman et al. "Chitin oligosaccharides can induce cortical cell division in roots of Vicia sativa when delivered by ballistic microtargetting". Development. 124: 4887-4895. 1997.*

Röhrig et al. "Growth of Tobacco Protoplasts Stimulated by Synthetic Lipo-Chitooligosaccharides". Science. 269:841-843. 1995.*

F.D. Dakora et al.; "Diverse functions of isoflavonoids in legumes transcend anti-microbial definitions of phytoalexins"; *Physiological and Molecular Plant Pathology*; 1996; vol. 49, pp. 1-20.

Anke J. De Jong, et al.; "Rhizobium Lipooligosaccharides Rescue a Carrot Somatic Embryo Mutant"; *The Plant Cell* Jun. 1993; vol. 5, pp. 615-620.

Jean Denarie, et al.; "Rhizobium Lipo-Chitooligosaccharide Nodulation Factors: Signaling Molecules Mediating Recognition and Morphogenesis"; *Annu. REv. Biochem.*; 1996; pp. 503-535.

Stephen C. Fry, et al.; "Oligosaccharides as Signals and Substrates in the Plant Cell Wall"; *Plant Physiol.*; 1993; pp. 1-5.

William K. Gillette, et al.; "Bradyrhizobium (Arachis) sp. Strain NC92 contains Two nodD Genes Involved in the Repression of nodA and a nolA Gene Required for the Efficient Nodulation of Host Plants"; *Journal of Bacteriology*; May 1996; pp. 2757-2766.

Renze Heidstra, et al.; "Nod factor-induced host responses and mechanisms of Nod factor perception"; *New Phytol*; 1996; vol. 133, pp. 25-43, 1995.

Sharon R. Long; "Rhizobium-Legume Nodulation: Life Together in the Underground"; *Cell*; Jan. 27, 1989; vol. 56, pp. 203-214.

Sharon R. Long; "Rhizobium Symbiosis: Nod Factors in Perspective"; *The Plant Cell*; Oct. 1996; vol. 8, pp. 1885-1898.

Jan-Peter Nap, et al.; "Developmental Biology of a Plant-Prokaryote Symbiosis: The Legume Root Nodule"; *Science*; Nov. 1990; vol. 250, pp. 948-954.

N. Kent Peters, et al.; "A Plant Flavone, Luteolin, Induces Expression of Rhizobium meliloti Nodulation Genes"; *Science*; Aug. 1986; vol. 233, pp. 977-980.

N.K. Peters, et al.; "Phenolic Compounds as Regulators of Gene Expression in Plant-Microbe Interactions"; *Molecular Plant-Microbe Interactions*; 1990; vol. 3, No. 1, pp. 4-8.

Horst Rohrig, et al.; "Growth of Tobacco Protoplasts Stimulated by Synthetic Lipo-Chitooligosaccharides"; *Science*; Aug. 1995; vol. 269, pp. 841-843.

Herman P. Spaink; "The Molecular Basis of Infection and Nodulation by Rhizobia: The Ins and Outs of Sympathogenesis"; *Annu. Rev. Phytopathol.*; 1995; vol. 33, pp. 345-368.

G. Stacey, et al.; "Signal Exchange in the Bradyrhizobium-Soybean Symbiosis"; *Soil Biol. Biochem*; 1995; vol. 27, pp. 473-483.

Gary Stacey; "Bradyrhizobium japonicum nodulation genetics"; *FEMS Microbiol. Lett*, 1995; vol. 127, pp. 1-9.

Thomas J.W. Stokkermans, et al.; "Structural Requirements of Synthetic and Natural Product Lipo-Chitin Oligosaccharides for Induction of Nodule Primordia on Glycine soja"; *Plant Physiol.*; 1995; vol. 108, pp. 1587-1595.

Georges Truchet, et al.; "Suphated lipo-oligosaccharide signals of Rhizobium meliloti elicit root nodule organogenesis in alfalfa"; *Nature*; Jun. 20, 1991; vol. 351, pp. 670-673.

Desh Pal S. Verma; "Signals in Root Nodule Organogenesis and Endocytosis of Rhizobium"; *The Plant Cell* Apr. 1992; vol. 4, pp. 373-382.

Ronald W. Wilen, et al.; "Interaction of abscisic acid and jasmonic acid on the inhibition of seed germination and the induction of freezing tolerance"; *Can. J. Bot.*; 1994; vol. 72, pp. 1009-1017.

Feng Zhang, et al.; Preincubation of Bradyrhizobium japoncium with Genistein Accelerates Nodule Development of Soybean at Suboptimal Root Zone Temperatures; *Plant Physiol*; 1995; vol. 108, pp. 961-968.

Feng Zhang, et al.; "Inhibition of the Expression of Bradyrhizobium Japonicum Nod genes at low temperatures-"*Soil Biol. Biochem.*; 1996; vol. 28, No. 12, pp. 1579-1583.

Chemical Abstracts, vol. 125, No. 23, Dec. 2, 1996; abstract No. 297004, Spaink, Herman P.; "Regulation of Plant morphogenesis by lip-chitin oligosaccharides"; Crit. Rev. Plant Sci.

Database Caba 'Online!; Stokkermans et al.; "Structure requirement of synthetic and natural product lipo-chitin oligosaccharides for induction of nodule primordia on Glycine soja"; Plant Physiology; vol. 108, No. 4, 1995.

Database Caba 'Online!; Autun; "Potential of Rhizobium and Bradyrhizobyum species as plant growth promoting rhizobacteria on non-legumes: effect on radishes"; Plant and soil; vol. 204, No. 1, 1998.

E.C. Cocking et al.; "Interaction of Rhizobia with non-legume crops for symbiotic nitrogen fixation nodulation", Nato Asi Series. Series G:Ecological Sciences; vol. G37, pp. 197-205.

Database Caba 'Online!; Zaidi et al.; "Growth regulators-mediated biological nitrogen fixation in soybean under salt stress conditions"; Indian Journal of Plant Physiology; vol. 3, No. 3, 1998.

* cited by examiner

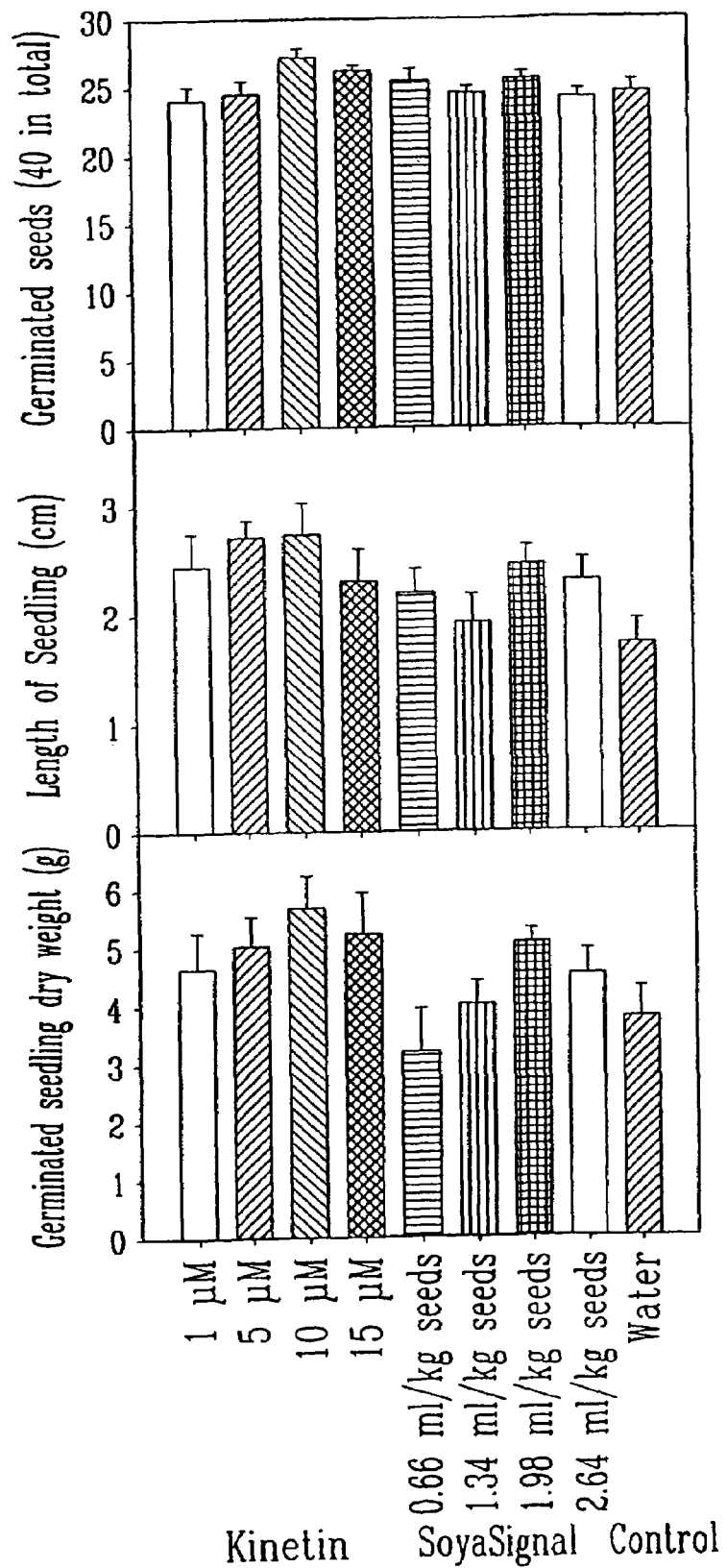

COMPOSITION FOR ACCELERATING SEED GERMINATION AND PLANT GROWTH

FIELD OF THE INVENTION

The present invention relates to agriculture. More specifically, the invention relates to plant seed germination, seedling emergence, quiescence-breakage and plant growth. Even more specifically, the present invention relates to compositions which accelerate plant seed germination, seedling emergence and plant growth of numerous types of crops and to methods using same.

BACKGROUND OF THE INVENTION

Symbiotic microorganisms can promote the growth of legumes by way of biological fixation of nitrogen. More specifically, rhizobiaceae are gram-negative soil bacteria which fix nitrogen and are involved in symbiotic association with these legumes. This symbiotic association between the bacteria and the legume enables the latter to grow in soils having low assimilable nitrogen levels. In return, through photosynthesis, the legume provides the bacteria with the energy it requires to reduce the atmospheric nitrogen into ammonia. This ammonia can then be used by the legume and enters into the nitrogen metabolism. The legume, of the Fabaceae family, forms nodules in which the rhizobia proliferate. The Rhizbiaceae family is in a state of taxonomic flux. It has been reported to comprise four main genera: *Rhizobium, Bradyrhizobium, Sinorhizobium* and *Azorhizobium* (U.S. Pat. No. 5,549,718). The symbiotic relationship between nitrogen-fixing bacteria or rhizobia and plants of the Fabaceae family enables the growth of the latter in soils having low levels of available nitrogen, thus reducing the need for nitrogen fertilizers. Since nitrogen fertilizers can significantly increase the cost of crops, and are associated with a number of polluting effects, biological means to stimulate this symbiotic relationship and/or to decrease the use of nitrogen fertilizers is of great importance.

Initial recognition between *B. japonicum* and soybean involves exchange of molecular signals (Stacey et al, 1995). Legume roots secrete phenolic compounds (Dakora & Philips, 1996; Peters & Verma, 1990), largely from the area of root hair emergence, which act as chemo-attractants to (brady)rhizobia (Nap & Bisseling, 1990), and activate the nod genes. Flavones, isoflavones, and flavanones have been identified as the inducing molecules for (brady)rhizobial chemotaxis and for expression of nod genes, e.g. genistein, daidzein and several related compounds in soybean (Peters & Verma, 1990). These plant-to-bacteria signal compounds cause expression of the bacterial nod (also nol and noe) genes very rapidly (only a few minutes after exposure) and at very low concentrations ($10^{-7}$ to $10^{-8}$ M) (Peters et al., 1986). Generally this is through an interaction with nodD, which activates the common nod genes, although the situation may be more complex, as is the case in *B. japonicum*, where $nodD_1$, $nodD_2$ and nodVW are involved (Gillette & Elkan 1996; Stacey 1995). Nod genes have been identified in the rhizobia that form nitrogen fixing relationships with numbers of the Fabaceae family (see U.S. Pat. No. 5,549,718 and references therein). Recently, the plant-to-bacteria signal molecules have been shown to promote soybean nodulation and nitrogen fixation under cool soil temperatures (CA 2,179,879) and increase the final soybean grain yield on average of 10% in the field and up to 40% under certain conditions.

Among the products of the nod genes induced by the plant phenolic signal molecules are various enzymes involved in the synthesis of a series of lipo chitooligosaccharides (LCOs) (Spaink, 1995; Stacey, 1995). These newly synthesized LCOs act as bacterium-to-plant signals, inducing expression of many of the early nodulin genes (Long, 1989). This results in root hair deformation (including curling), cortical cell division leading to initiation of nodule meristems, secretion of additional nod gene inducers, and initiation of infection threads (Verma, 1992). These bacterium-to-plant signals exert a powerful influence over the plant genome and, when added in the absence of the bacteria, can induce the formation of root nodules (Truchet et al., 1991). Thus, the bacteria-to-plant signals can, without the bacteria, induce all the gene activity for nodule organogenesis (Denarie et al., 1996; Heidstra & Bisseling, 1996). Moreover, the above-mentioned activities induced by LCOs can be produced by concentrations as low as $10^{-14}$ M (Stokkermans et al. 1995). The mutual exchange of signals between the bacteria and the plant are essential for the symbiotic interaction. *Rhizobia* mutants unable to synthesize LCOs will not form nodules. Analysis of the *B. japonicum* nod genes indicates that ability to induce soybean nodulation requires at least: 1) a basic tetrameric Nod factor requiring only nodABC genes or 2) a pentameric LCO(C18:1, C16:0 or C16: fatty acid and a methyl-fucose at the reducing end, sometimes acetylated) requiring nodABCZ genes (Stokkermans et al. 1995).

When added to the appropriate legume, LCOs can cause the induction of nodule meristems (Denarie et al., 1996), and therefore cell division activity. One previous publication has shown that LCOs can induce cell cycle activities in a carrot embryogenesis system at levels as low as $10^{-14}$ M (De Jong et al. 1993).

A chemical structure of lipo chitooligosaccharides, also termed "symbiotic Nod signals" or "Nod factor", has been described in U.S. Pat. Nos. 5,549,718 and 5,175,149. These Nod factors have the properties of a lectin ligand or lipo-oligosaccharide substances which can be purified from bacteria or synthesized or produced by genetic engineering.

The relationship between environmental variables, such as low root zone temperature (RZT) and pH, and the interplay of molecular signals has only recently become a subject of investigation. For example, some soybean genotypes have less synthesis abilities for isoflavones under cool soil temperature, whereas a higher isoflavone concentration is needed to turn on the nod genes of *B. japonicum* (Zhang and Smith 1995 and 1997). The plant-to-bacteria signal molecules (i.e. isoflavones) have been shown, among other things, to overcome the negative effect of low temperature on the early events of symbiotic nitrogen fixation (Canadian application number 2,179,879).

While the effects of plant-to-bacteria signal molecules (i.e. isoflavones) on nodulation, nitrogen fixation, growth and protein yield of legumes, such as soybean, and on bacteria-to-plant signal molecules (LCOs) on nodulation and nitrogen fixation in legumes have been described under certain conditions, the effect of the bacteria-to-plant signal molecules on the growth of non-legumes is unknown. In fact, the role of such bacteria-to-plant signal molecules on non-legumes has never been assessed. In addition, the effect of LCOs on processes other than nodulation of legumes has yet to be studied.

There thus remains a need to assess the effect of LCOs on seed germination, seedling emergence and/or growth of plants in general and especially of non-legume plants.

The present invention seeks to meet these and other needs.

The present description refers to a number of documents, the contents of which are herein incorporated by reference in their entirety.

SUMMARY OF THE INVENTION

The invention concerns a composition for enhancing seed germination, seedling emergence and growth of plants and especially of crop plants. More specifically, the present invention relates to a composition comprising an LCO which can increase seed germination and/or seedling emergence and/or growth of a legume, in addition to acting as a trigger to initiate legume symbiotic nitrogen fixation. More particularly, the invention relates to increased seed germination and/or seedling emergence and/or growth of soybean, pea and red clover.

Surprisingly, the compositions of the present invention act not only on legumes such as soybean but on plants in general as exemplified with non-legume crops from different plant families Poaceae, Cucurbitaceae, Malvaceae. Asteraceae, Chenopodiaceae and Solonaceae. More specifically, the non-legume crops exemplified herein include corn, cotton, cantaloupe, cucumber, canola, lettuce, potato and beet. The present invention thus also refers to compositions for enhancing seed germination and/or seedling emergence and/or growth of non-legumes. More particularly, the invention relates to compositions comprising an LCO for enhancing seed germination, seedling emergence and growth of non-legumes. Non-limiting examples of such non-legumes include cotton, corn, canola, potato, cucumber, cantaloupe, lettuce and beet. Broadly, the present invention relates to compositions comprising an LCO for promoting growth of a crop. Non-limiting examples of crop plants include monocot, dicot, members of the grass family (containing the cereals), and legumes.

Thus, the present invention relates to agricultural compositions comprising at least one LCO (and methods of using same) for promoting seed germination, and/or early development of seedlings, and/or emergence of sprouts from tubers, and/or rapid development of new plants from higher plant perinating structures.

In a particular set of experiments in the field, a composition of the present invention comprising an LCO was shown to significantly enhance early plant growth.

The invention in addition relates to methods for enhancing seed germination and/or seedling emergence and/or growth of plants and/or for breaking the dormancy thereof comprising a treatment in the vicinity of a seed or seedling or plant with an effective amount of an agricultural composition comprising an LCO and an agriculturally suitable carrier for a sufficient time and under conditions which enable an increased germination of the seed and/or an increased emergence of the seedling and/or an increased growth of the plant and/or a triggering of the growth of a dormant plant.

The invention also relates to compositions and methods for breaking the dormancy of a plant and initiating the growth thereof. In a particular embodiment, the invention relates to the breaking of dormancy of potato.

The Applicant is the first to show that a composition comprising an LCO can have a significant effect on seed germination, and/or seedling emergence of legumes. Moreover, the Applicant is the first to show the surprising effect of signal molecules involved in bacteria-legume signalling on the growth of non-legume plants. In addition, the Applicant is the first to show that a composition comprising an LCO had an effect on non-legume seed germination and/or seedling emergence and/or plant growth of the non-legume. Also, the Applicant is the first to show that an LCO can not only act as a dormancy breaker but that it can also significantly increase the yield of a dormant plant following the dormancy breakage, when compared to known dormancy breakers.

While the seed germination and/or seedling emergence and/or plant growth enhancing capabilities of the compositions of the instant invention are demonstrated with corn, cotton, canola, potato, cantaloupe, lettuce, beet, cucumber, soybean, pea and red clover, they are applicable to plants in general and more especially to crop plants. Indeed, the plants chosen for the experiments presented herein are crops from significantly divergent plants in eight distinct families: (1) corn, the only monocot tested herein, in the family of grasses (Poaceae), which also contains the cereals; (2) cucumber and cantaloupe, the latter being a plant used horticulturally, and being slow to germinate at low temperature [its base temperature is about 14° C.] (Cucurbitaceae); (3) cotton, one of the most important fibre crops on the planet (Malvaceae); (4) lettuce (Asteraceae); (5) beet (Chenopodiaceae); (6) potato, a very important crop (Solonacea, which also includes tobacco, peppers and tomato); and two families of legumes (7) canola, representing the mustard group (Brassicaceae) and (8) soybean (representative of oil seed crop), bean (representative of a crop for human consumption) and red clover and alfalfa (forage legumes) (all of the Fabaceae family).

In view of the diversity of the plants tested, and of the similar results obtained with these different crop plants, it can be predicted that such results will apply to crop plants in general. It follows that a person skilled in the art can adapt the teachings of the present invention to other crops. Non-limiting examples thereof include tobacco, tomato, wheat, barley, rice, sunflower and plants grown for flower production (daisy, carnation, pansy, gladiola, lilies and the like). It will be understood that the compositions can be adapted to specific crops, to meet particular needs.

In accordance with the present invention, there is thus provided an agricultural composition for enhancing plant crop seed germination and/or seedling emergence and/or growth of a plant crop comprising a growth-promoting amount of at least one lipo chitooligosaccharide (LCO) together with an agriculturally suitable carrier. There is also provided a composition for breaking the dormancy and/or quiescence of a plant, comprising a growth-promoting amount of at least one lipo chitooligosaccharide (LCO) together with an agriculturally suitable carrier. Furthermore, there is provided a method for enhancing seed germination and/or seedling emergence and/or growth of a plant, comprising a treatment in the vicinity of one of a seed, root or plant with a composition comprising an agriculturally effective amount of a lipo chitooligosaccharide (LCO) in admixture with an agriculturally suitable carrier medium, wherein the effective amount enhances seed germination and/or seedling emergence and/or growth of the plant in comparison to an untreated plant. There is further provided a method for enhancing seed germination and/or seedling emergence and/or growth of a plant crop comprising incubating a rhizobial strain which expresses a lipo chitooligosaccharide (LCO) in the vicinity of one of a seed and/or root of the plant such that the LCO enhances seed germination and/or seedling emergence and/or growth of the plant crop.

As used herein, the term "rhizobia" is used broadly to refer to bacterial strains which are involved in a nitrogen fixing symbiotic relationship with a legume.

As used herein, the term "LCO" refers broadly to a Nod factor which is under the control of at least one nodulation gene (nod gene), common to rhizobia. LCO therefore relates to a bacteria-to-plant signal molecule which induces the formation of nodules in legumes and enables the symbiotic bacteria to colonize same. Broadly, LCOs are lipo chitooligosaccharide signal molecules, acting as phytohormones, comprising an oligosaccharide moiety having a fatty acid condensed at one of its end. An example of an LCO is presented below as formula I

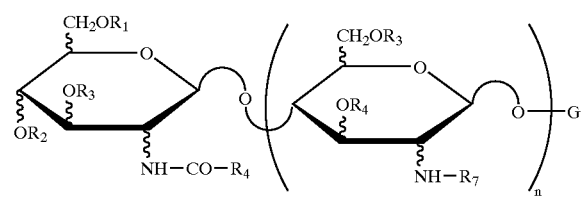

in which:

G is a hexosamine which can be substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3CO-$, $C_xH_yCO-$ where x is an integer between 0 and 17, and y is an integer between 1 and 35, or any other acyl group such as for example a carbamyl, $R_4$ represents a mono-, di- or triunsaturated aliphatic chain containing at least 12 carbon atoms, and n is an integer between 1 and 4.

More specific LCOs from *R. meliloti* have also been described in U.S. Pat. No. 5,549,718 as having the formula II Even more specific LCOs include NodRM, NodRM-1, NodRM-3. When acetylated (the $R=CH_3CO-$), they become AcNodRM-1, and AcNodRM-3, respectively (U.S. Pat. No. 5,545,718).

LCOs from *B. japonicum* have also been characterized in U.S. Pat. Nos. 5,175,149 and 5,321,011. Broadly, they are pentasaccharide phytohormones comprising methylfucose. A number of these *B. japonicum*-derived LCOs are described: BjNod-V ($C_{18:1}$); BjNod-V ($A_C$, $C_{18:1}$), BjNod-V ($C_{16:1}$); and BjNod-V ($A_C$, $C_{16:0}$), with "V" indicating the presence of five N-acetylglucosamines; "Ac" an acetylation; the number following the "C" indicating the number of carbons in the fatty acid side chain; and the number following the ":" the number of double bonds.

It shall also be understood that compositions comprising different LCOs, are encompassed within the scope of the present invention. Indeed, while the present invention is exemplified with NodBj-V($C_{18:1A}$)11 also known as BjNod-V($C_{18:1}$MeFuc); NodRM-V($C_{16:2}$, S); and NodRI, any LCO produced by a rhizobia which is capable of entering into a nitrogen fixation relationship with a legume (i.e. a member of the Fabiaceae family) is expected to have the potential to show the same properties as those described herein. It will be clear to the person of ordinary skill that the selection of a rhizobia known to be expressing LCOs at high levels, or known to express an LCO having an effect on a broader spectrum of legumes could be advantageous.

It will also be clear that the LCO compositions of the present invention could also comprise more than one signal molecule. Non-limiting examples of such compositions include agricultural compositions comprising in addition to one LCO: (1) at least one additional LCO; (2) at least one plant-to-bacteria signal molecule; (3) gibberellic acid or other agents or compounds known to promote growth or fitness of plants; and mixtures of such compositions (1), (2) or (3).

It shall be clear that having identified new uses for LCO, bacteria could be genetically engineered to express nod

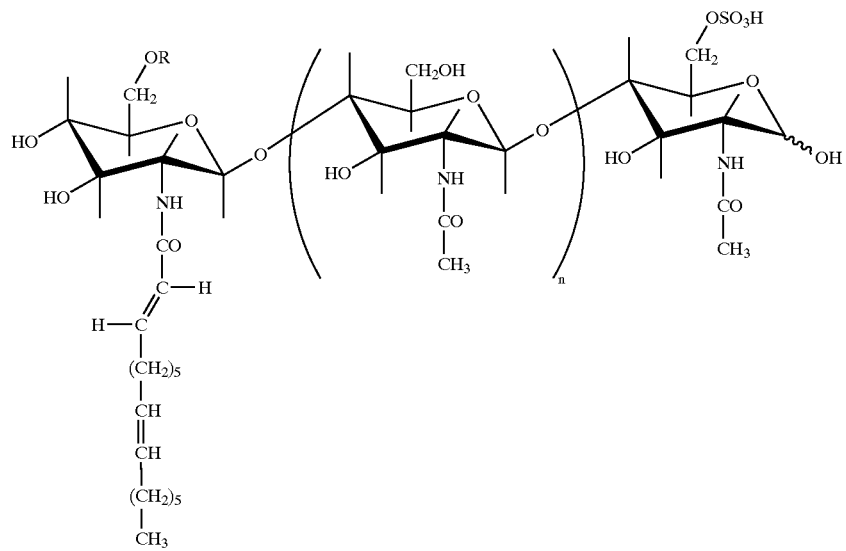

in which R represents H or $CH_3CO-$ and n is equal to 2 or 3.

genes and used for producing LCOs or for direct administration to the plants and/or seeds.

Thus, while the instant invention is demonstrated in particular with LCOs from *Bradyrhizobium japonicum*, *Rhizobium meliloti* and *R. leguminosarum* and selected legumes and non-legume crops, the invention is not so limited. Other legume crops, non-legume crops and rhizobial strains may be used using the same principles taught herein. Preferred matching of rhizobia with legume crop groups include, for example:

| rhizobial species | Legume crop group |
|---|---|
| R. meliloti | alfalfa, sweet clover |
| R. leguminosarum | peas, lentils |
| R. phaesolii | beans |
| Bradyrhizobium japonicum | soybeans |
| R. trifolii | red clover |

As will be apparent to the person of ordinary skill to which the present invention is directed, the growth-stimulating compositions of the present invention can be applied to other crop plants and especially to other warm climate adapted crop plants (plants or crops having evolved under warm conditions [i.e. tropical, subtropical or warm temperature zones] and whose metabolism is optimized for such climates). It should be understood that the growth-enhancing compositions of the present invention should find utility whenever a particular crop is grown in a condition which limits its growth. More particularly, whenever a particular plant crop is grown at a temperature which is below its optimum temperature for seed germination, seedling emergence, growth and the like. Such temperatures are known in the art. For example, optimum temperatures for germination of corn, soybean, rice and cotton are 30° C., 34–36° C., 30–32° C., and 34° C., respectively. The minimum germination temperatures (or base temperatures) for these crops are 9° C., 4° C., 8 to 10° C., and 14° C., respectively, while the maximum germination temperatures are 40° C., 42–44° C., 44° C. and 37° C., respectively. The compositions of the present invention therefore find utility, among other things, in enhancing germination of warm climate adapted crops when grown at temperatures between their base temperature for seed germination, and/or seedling emergence and/or growth and their optimum temperature for germination. The compositions of the present invention find utility in general in enhancing seed germination and/or se dling emergence and/or growth of crop plants when grown under conditions which delay or inhibit seed germination and/or seedling emergence thereof. Non-limiting examples of such inhibiting conditions (as known from their signalling inhibition in bacteria-legume interactions, their inhibition or delay of the bacteria-plant symbiotic relationship) include pH stress, heat-stress, and water stress.

It will be nevertheless recognized that the compositions and methods of the present invention enhance growth of plants grown under optimal conditions.

Thus, the compositions and methods of the present invention should not be limited to plants growing under suboptimal conditions.

The term "environmental conditions which inhibit or delay the bacterial-plant symbiotic relationship" should be interpreted herein as designating environmental conditions which postpone or inhibit the production and exchange of signal molecules between same and include, without being limited thereto: conditions that stress the plant, such as temperature stress, water stress, pH stress as well as inhibitory soil nitrogen concentrations or fixed nitrogen.

"An agriculturally effective amount of a composition" for increasing the growth of crop plants in accordance with the present invention refers to a quantity which is sufficient to result in a statistically significant enhancement of growth and/or of protein yield and/or of grain yield of the plant crop as compared to the growth, protein yield and grain yield of the control-treated plant crop. As will be seen below, the growth promoting activity of the LCOs are observable over a broad range of concentrations. Indeed, LCO growth-promoting activities can be observed at an applied concentration of about $10^{-5}$ to $10^{-14}$ M, preferably about $10^{-6}$ to about $10^{-12}$ M and more preferably about $10^{-7}$ to about $10^{-10}$M.

The term "immediate vicinity of a seed or roots" refers to any location of a seed or roots wherein if any soluble material or composition is so placed, any exhibit of the plant or of the bacteria, or bacterial cells will be in actual contact with the seed as it germinates or the roots as they grow and develop.

Direct or indirect methods of inoculation with the composition of the present invention can be employed. During direct inoculation the composition is applied directly to the seed prior to sowing. This can most simply be accomplished by spraying the seed with or dipping the seed into a liquid culture containing the desired components.

The recitation "short season condition" refers herein broadly to temperatures of the middle and temperate zones and shorter. Typically, the active growing season is around ½ to ⅔ of the year. Short season conditions broadly refers to a frost-free period of less than half the year, often on the order of 100 frost-free days.

By "nodulation gene-inducing" or "nod gene-inducing" is meant bacterial genes involved in nodule establishment and function.

By "seed germination" is meant a clear evidence of root growth developing from the embryo on the seed. When referring to an "increased seed germination", the Applicant refers to a significant difference in seed germination between the treated versus the control seed.

"Seedling emergence" is meant to refer to growth of the plant which is observable above the rooting medium surface. When referring to an "enhanced seedling emergence", the Applicant refers to a significant observable difference between the growth of the seedling in the treated versus the control.

BRIEF DESCRIPTION OF THE DRAWING

Having thus generally described the invention, reference will now be made to the accompanying drawing, showing by way of illustration a preferred embodiment thereof, and in which:

FIG. 1 shows the seed germination enhancing effect of a composition according to the present invention on corn.

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

While the effects on nodulation were detected upon treatment of soybean with SoyaSignal® (a composition comprising both the plant-to-bacteria and bacteria-to-plant signal molecules), it was also noted that in many of the field experiments the plants that received some sort of genistein treatment emerged from the soil sooner. Thus, an experiment, in which genistein alone, *B. japonicum* alone, and genistein plus *B. japonicum* were added to soybean seeds under controlled environment conditions, was conducted. Because slow germination of corn (and other plants, as well) is a serious agricultural problem in eastern Canada because the weather conditions limit the growth thereof, corn was also treated in a similar fashion. The experiment showed that the seed germination and seedling emergence promoting effect was present with the combination of genistein plus *B. japonicum*, leading to the conclusion that the enhancing effects were due to the LCOs produced by genistein exposed *B. japonicum*. Purification (HPLC and otherwise) of the LCO most abundantly produced by genistein-stimulated *B. japonicum* (NodBj-V($C_{18:1A}$11)) was carried out. This was aided by the gracious gift of enough LCO material to standardize the assay (G. Stacey, University of Tennessee at Knoxville; U.S. Pat. No. 5,175,149 and U.S. Pat. No. 5,321,011) which allowed both isolation and quantification. With isolated NodBj-V($C_{18:1A}$11), research on the ability of this compound to stimulate seed germination, seedling emergence and growth of leguminous and non-leguminous plants could be conducted.

These experiments surprisingly demonstrated that the addition of SoyaSignal (which comprises both an isoflavone and an LCO; the latter at a concentration of about 105M) accelerates the germination of corn seeds, whereas isoflavone solutions alone do not. Presumably this effect was due to the LCOs produced by *B. japonicum* cells and induced by the presence of isoflavones. When the seedlings were harvested (still at the mesocotyl stage) they were 44% longer and 33% as heavier in the genistein-*B. japonicum* treated versus non-treated plants (FIG. 1). In addition, not only did seedling emergence increase, but the rate of cotton seed germination was also accelerated by the application of SoyaSignal®. The germination rate of cotton seeds treated with SoyaSignal® (0.66 ml/kg seed) increased by 145% compared to those control seeds that were treated with pure water. Both the corn and cotton experiments were conducted at low temperatures, 15° C. and 17° C. for corn seeds and for cotton seeds, respectively.

The field trial showed that the time of tasselling of sweet corn treated with SoyaSignal® (planted on May 6 on the Experimental Farm of McGill University, Quebec) was 1 to 2 days earlier compared to that of untreated plants. Soybean seeds that received SoyaSignal® (planted on June 22 in Martinsville, Ill.) emerged 8 hours earlier compared to control seeds while the first trifoliar fully expanded 1 day earlier. At the agronomy farm of Purdue University, Ind., soybeans planted in early June and observed in early July were already one stage further in their development (V6) compared to the control plants (V5). In a farmer trial (in Jackson, Ill.), plants that received SoyaSignal® had many more nodules on the secondary roots and were 10% taller than untreated plants.

Thus, an LCO (a bacteria-to-plant signal molecule involved in the establishment of the symbiotic relationship between a rhizobia and a legume) can promote growth of corn, a monocot distantly related to legumes. Based on the evolutionary divergence of corn from legumes and the significant response thereof to the LCO treatments, corn was used as a model plant system in follow-up experiments. These experiments demonstrated that the results obtained with corn were also observable with all other crop plants tested.

Taken together, the laboratory data and field trials presented herein show that an LCO can increase seed germination, seedling emergence and plant growth of legumes and non-legume plants under controlled environment and field conditions.

The signal molecules are also shown to break the dormancy of potato tubers. Of note, the dormancy experiments showed that the signal solution was better at increasing the yield of potato tubers as compared to other dormancy breakers (i.e. giberellic acid).

The precise mechanism of action of LCOs on seed germination, seedling emergence dormancy and plant growth of legumes and non-legumes is not fully understood. The general understanding of the role of LCOs in signalling during the establishment of the legume-rhizobia symbiosis was described above. When added to the appropriate legume, LCOs can cause the induction of nodule meristems. Thus, it is possible that LCOs might be normal signal molecules in higher plants, so that exogenously supplying them simply increases their levels and, therefore, the activity of the things they would normally regulate. Alternatively, there may be an endogenous class of signal molecules which play important roles in plant development, and have a conformation similar to those of LCOs. One possible candidate for this is the oligosaccharins (Fry et al. 1993), some of which do stimulate meristem activity (Pavlova et al. 1992). LCOs are somewhat similar in structure and chemistry to the oligosaccharins (Fry et al. 1993) and can, in the broadest sense, be included in that group (Stokkermans et al. 1995). However, the signal molecules with a similar conformation need not be chemically similar, as demonstrated by the ability of opiates (plant alkaloids) to fit into receptor sites normally occupied by endorphrins (oligo-peptides). Nothing is known regarding the mechanisms by which LCOs cause this activity. Without being limited to a particular theory, the present invention is nevertheless the first to have identified a seed germination, and/or seedling emergence and/or dormancy breaking and/or plant growth promoting effect of a composition comprising LCOs on non-legume plants.

Crops, such as soybean, corn and cotton evolved in relatively warm climates and, as a result, have high base temperatures for germination, being of about 5° C. for soybean, 10° C. for corn and 14° C. for cotton. These high base germination temperatures lead to slow emergence after planting, resulting in slow leaf ground cover early in the season (when the temperature is sub-optimal), which in turn leads to poorer early season light interception, poorer competition with weeds (and therefore greater need for herbicide application) and increased soil erosion during heavy rainfall events. To simplify, these crops are often grown under conditions which limit their seed germination, and/or seedling emergence and/or growth. Hence, the use of a growth-promoting factor which is in limiting amount can compensate for a deficiency or stress in the growth conditions. Using SoyaSignal® as a plant growth regulator could thus partially overcome the negative effects of environmental stress conditions, such as low soil temperature on crop seed germination, seedling emergence and plant development. Thus, the present invention provides the means to improve the production of crops of tropical and subtropical origin in the temperate zones and may extend their production into shorter season areas. In addition, the present invention provides the means to improve production of crops growing under stress conditions.

The present invention is illustrated in further detail by the following non-limiting examples.

EXAMPLE 1

Induction of LCO Production by *Bradyrhizobium japonicum*

The first culture containing *Bradyrhizobium japonicum* (strain 532C) was grown at 28° C. in 100–125 mL of sterile yeast mannitol media (YEM) with pH 6.8, shaken at 150 rpm until the $OD_{620}$ reaches 0.4–0.6 (4–6 days). Thereafter, a 2L bacterial subculture was started by inoculating with material from the first culture (5 mL of first culture per 250 mL of YEM media), for 5–7 days ($OD_{620}$~0.8–1.0), as above. At this stage, 0.25 L of 50 $\mu$M genistein (in methanol) were added to each 250 mL of bacterial subculture (genistein concentration of 5 $\mu$M) and the culture was incubated for 48–96 hours, the flavone thereby inducing LCO production in the bacterial cells.

EXAMPLE 2

Induction of LCO production by *Rhizobium meliloti* or *Rhizobium leguminosarum*

The first culture of *Rhizobium meliloti* strain RCR2011 was grown at 28° C. in 100–125 mL of sterile yeast mannitol media (YEM) with pH 6.8, shaken at 150 rpm until the $OD_{620}$ reaches 0.4–0.6 (2–3 days). Thereafter, a 2L bacterial subculture was started by inoculating first culture (5 mL of first culture per 250 mL of YEM media), for 2–3 days ($OD_{620}$~0.8–1.0), as above. At this stage, 0.25 mL of 50 $\mu$M luteolin (in methanol) was added to each 250 mL of bacterial subculture (luteolin concentration of 5 $\mu$M) and the culture was incubated for 48 hours, the flavone thereby inducing LCO production in the bacterial cells.

For LCO production by *Rhizobium leguminosarum*, the rhizobia was grown similarly as above. The flavone (naringenin) was added to the subculture of *R. leguminosarum* (10 $\mu$M) and the procedure carried out as above.

EXAMPLE 3

Extraction and Purification of LCOs

Two liters of bacterial subculture were phase-partitioned against 0.8 L of HPLC-grade 1-butanol by shaking overnight. The upper butanol layer was then transferred to a 1 L evaporation flask and evaporated at 80° C. to 2–3 mL of light brown, viscose material with a Yamato RE500 Rotary Evaporator, which was resuspended in 4 mL of 18% acetonitrile and kept in the dark at 4° C. in a sealed glass vial.

HPLC analysis was conducted with a Vydac C18 reversed-phase column with flow rate 1.0 mL/min and a Vydac guard column. As a baseline, acetonitrile ($AcN/H_2O$; w/w) was run through the system for at least 10 min. When the sample was loaded, an isocratic elution was started by 18% of AcN for 45 min. This step aims at removing all non-polar contaminant light fractions. Thereafter, a gradient elution for 90 min. with 18–82% AcN was performed. LCOs began to elute after 94–96 min. of HPLC run time.

For the purification of LCOs from *R. leguminosarum* (which nodulates numerous legumes), the HPLC peaks were identified and compared to those obtained with *B. japonicum* and *R. meliloti*. LCO peaks which were different from those of these two other rhizobia were identified collected. Thus, it is strongly suggested that the *R. leguminosarum* LCOs used herein are different from that of *B. japonicum* or *R. meliloti*.

EXAMPLE 4

Effect of LCO on Emergence of Some Plant Species

Plastic pots (7.5 cm dia) were filled with 15 g of autoclaved vermiculite. Seeds of corn (*Zea mays*—Poaceae), bean (*Phaseolus vulgaris*—Fabaceae), canola (*Brassica napus*—Brassicaceae), cucumber (*Cucumis sativus*—Cucurbitaceae), cantaloupe (*Cucumis melo*—Cucurbitaceae), cotton (*Gossypium* sp.—Malvaceae), lettuce (*Lactuca sativa*—Asteraceae), beet (*Beta vulgaris*—Chenopodiaceae), and soybean (*Glycine max*—Fabaceae), were placed at 2.5 cm deep at the rate of 5 or 10 seeds per pot. Pots were irrigated with either 25 mL of LCO solution at different concentrations ($10^{-6}$–$10^{-14}$M) or aqueous acetonitrile or water, as controls. Acetonitrile was included as one of the controls since LCO was purified in this solvent (see Example 3), after 4 days the pots were irrigated with 10 mL of water once every two days. Each treatment had 4 replications in a randomized block design. Pots were placed on a green house bench maintained at 25±2° C. with a day/night cycle 16/8 h and relative humidity of 70%, or in a growth chamber set at 15° C. with a 16:8 day/night cycle.

As defined above, seed germination has occurred when clear evidence of root growth developping from the embryo on the seed is observed.

As the time required for seedling emergence of the species used in the experiment varied considerably, observation on seedling emergence was recorded when the emergence was observed for at least 50% in most of the treatments. As defined above, seedling emergence has occurred when growth of the plant can be observed above the rooting medium surface. The percent emergence was calculated. The data were analyzed with Statistical Analysis System, version 6.12 (SAS institute Inc. Cary, N.C., USA).

LCO treatment reduced the time required from sowing to emergence of a number of economically important plant species tested. Among the species tested, *Z. mays, L. sativa, B. vulgaris, P. vulgaris*, and *G. max* showed significant increases in emergence when treated with LCO at 25° C. (Table 1), while, *C. sativus* and *B. napus* showed similar effects at 15° C. (Table 2).

TABLE 1

Effect of lipo chitooligosaccharide on seedling emergence (%) at 25° C.

| Treatment | Zea mays | Beta vulgaris | Glycine max | Gossypium sp. | Cucumis melo | Letuca sativa | Phaseolus vulgaris |
|---|---|---|---|---|---|---|---|
| Control | 40 c[Ψ] | 33 a | 40 e | 55 b | 80 a | 5 d | 44 abc |
| $10^{-6}$ M | 76 ab | NT | 65 d | 88 a | NT | 45 a | 67 abc |
| $10^{-7}$ M | 68 abc | 66.6 | 80 bc | 66 ab | 100 b | 35 ab | 89 a |
| $10^{-8}$ M | 84 a | NT | 90 ab | 88 a | NT | 10 dc | 78 ab |
| $10^{-9}$ M | 88 a | 66 b | 100 a | 88 a | 100 b | 20 bcd | 67 abc |
| $10^{-10}$ M | 84 a | NT | 70 cd | 88 a | NT | 25 abcd | 44 abc |
| $10^{-11}$ M | 68 abc | 86 b | 50 e | NT | 100 b | 26 abcd | 22 c |
| $10^{-12}$ M | 48 abc | NT | 80 bc | NT | NT | 30 abc | 33 bc |
| $10^{-13}$ M | 40 c | 80 b | 70 cd | NT | 100 b | 5 d | 33 bc |
| $10^{-14}$ M | 40 c | NT | 70 cd | NT | NT | 10 d | 33 bc |

[Ψ]means with in the same column, followed by the same letter are not significantly different (p ≤ 0.05) by ANOVA protected LSD test.
NT - Not tested

TABLE 2

Effect of lipo chitooligosaccharide on seedling emergence at 15° C.

| Treatment | Cucumis sativus | Brassica napus |
|---|---|---|
| Control | 60 c[Ψ] | 32.5 c |
| Lipo chitooligosaccharide | | |
| $10^{-6}$M | 65 abc | 35 bc |
| $10^{-7}$M | 85 ab | 32 c |
| $10^{-8}$M | 80 ab | 35 bc |
| $10^{-9}$M | 70 abc | 52 ab |
| $10^{-10}$M | 50 c | 62 a |
| $10^{-11}$M | 80 ab | 47 bc |
| $10^{-12}$M | 80 ab | 45 bc |
| $10^{-13}$M | 70 abc | 37 bc |
| $10^{-14}$M | 70 abc | 30 c |

[Ψ]means with in the same column, followed by the same letter are not significantly different (p ≤ 0.05) by ANOVA protected LSD test.

In some plants, germination/emergence promoting effects of LCOs is seen at all temperatures suitable for growth, while in others, it is only observed under temperature-limiting conditions.

EXAMPLE 5

Effects of LCO on Early Growth of Corn

The percent seedling emergence was recorded at 4 days after sowing (DAS). Plant height was recorded from 4 DAS to 15 DAS. Plants were harvested at 15 DAS and leaf area, root length and the number of roots per plant were recorded. The plants were then dissected and placed in paper covers and dried at 90° C. for 24 h and the dry weights of roots, shoots and the spent seeds recorded. The data were analyzed with the Statistical Analysis System version 6.12 (SAS institute Inc. Cary, N.C., USA).

In LCO treatments, seedling emergence started 2–3 days after seeding while in the control it was 3–4 days. LCO treatments significantly increased leaf area, root length, number of roots, shoot dry weight and root dry weight, while the weight of spent seed recorded significant decreases as compared to the control (Table 3). The optimum effect was observed at an LCO concentration of $10^{-8}$M. The decrease in spent seed weight is attributed to the rapid translocation of stored reserve from the seed endosperm to the embryo. Of interest, a dramatic increase of α-amylase activity was observed in the treated seeds.

TABLE 3

Effect of lipo chitooligosaccharide on early growth (after seedling emergence) of Zea mays

| Treatment | Leaf area (cm²) | Root length (mm) | No. of roots | Plant height at 15 DAS (mm) | Root dry wt./plant (mg) | Spent seed dry wt. (mg) | Shoot dry wt./plant (mg) |
|---|---|---|---|---|---|---|---|
| Water | 5.81 f[Ψ] | 103.1 e | 5.1 e | 79.8 d | 53.2 de | 163.6 a | 28.8 e |
| Acetonitrile | 7.63 ef | 106.3 e | 5.8 de | 94.1 cd | 65.4 e | 147.4 ab | 30.1 de |
| LCO 10-5 | 11.7 cd | 137.0 cd | 6.8 cd | 102.9 c | 75.7 cd | 123.5 bc | 41.6 bcd |
| LCO 10-6 | 18.2 a | 150.8 bc | 7.66 abc | 130.4 ab | 85.1 bc | 90.7 cd | 51.4 b |
| LCO 10-7 | 15.7 ab | 153.9 b | 8.0 ab | 130.1 ab | 96.5 ab | 99.5 cd | 51.6 b |
| LCO 10-8 | 19.3 a | 187.0 a | 8.4 a | 142.6 a | 103.4 a | 76.3 d | 66.2 a |
| LCO 10-9 | 17.0 ab | 144.4 cbd | 7.75 abc | 134.7 ab | 83.3 bc | 93.7 cd | 46.8 bc |
| LCO 10-10 | 13.9 bc | 149.1 bc | 7.95 ab | 127.1 b | 89.5 abc | 89.8 cd | 51.4 b |
| LCO 10-11 | 8.51 def | 132.1 d | 6.69 cd | 103.3 | 74.6 cd | 115.9 bc | 38.0 cde |
| LCO 10-12 | 8.0 def | 137.9 cd | 7.25 d | 98.3 c | 84.6 bc | 105.4 od | 40.6 bcde |

TABLE 3-continued

Effect of lipo chitooligosaccharide on early growth (after seedling emergence) of Zea mays

| Treatment | Leaf area (cm²) | Root length (mm) | No. of roots | Plant height at 15 DAS (mm) | Root dry wt./plant (mg) | Spent seed dry wt. (mg) | Shoot dry wt./plant (mg) |
|---|---|---|---|---|---|---|---|
| LCO 10⁻¹³ | 10.4 cde | 130.9 d | 6.7 cd | 91.8 cd | 85.4 bc | 109.6 cd | 43.6 bc |
| LCO 10⁻¹⁴ | 11.2 cde | 136.8 cd | 7.36 abc | 99.9 c | 90.2 abc | 102.9 cd | 46.6 bc |

ᵠmeans with in the same column, followed by the same letter are not significantly different ($p \leq 0.05$) by ANOVA protected LSD test.

Taken together, Examples 4 and 5 and Tables 1–3 show that LCOs can stimulate seedling emergence in all tested plants. In addition, a significant growth stimulation of corn was observed. Furthermore, the spent seed weight results suggested that LCOs also had an effect on seed germination for all tested plants. The growth-promoting effect of LCOs on corn, a plant quite distantly related to legumes (i.e. corn is a monocot), strongly suggests that plants in general should show the same growth-responses to LCO treatment.

EXAMPLE 6

Dormancy Breaking Activity of LCO on Potato Mini Tubers

Signal solution is a bacterial fermentation tank product, comprising approximately $10^{-4}$ M LCO from *B. japonicum*. More specifically, signal solution is the supernatant from a culture of *B. japonicum* in which genestein (a flavone) had been introduced to promote LCO expression. Following the subculture of *B. japonicum*, the bacteria was removed. While the stimulatory effect of Signal solution in the soybean-*Bradyrhizobium* japonicum complex has been described (Zhang and Smith, 1995; Zhang et al. 1996), the effects of these plant substances in other plant species and their associated rhizospheres' organisms have not been investigated.

Gibberellic acid (GA) and kinetin affect both the germination rate and the percent germination of crop seeds.

Some studies have indicated that plant growth regulators (PGRs), such as gibberellic acids (GAs), stimulate seed germination at low temperatures. Durrant and Mash (1991) reported that adding gibberellins ($GA_{4/7}$) to sugar-beet seeds (*Beta vulgaris* L. Var. *altissima*) was beneficial to seed germination under cold, wet conditions.

Kepczynski and Bialecka reported that Methyl jasmonate (JA-Me) inhibited or retarded germination of *Amaranthus caudatus* seeds in darkness at 24° C. Ethephon, ACC (1-aminocyclopropane-1-carboxylic acid) and gibberellins ($GA_3$ or $GA_{4+7}$) partially or completely reversed this inhibition depending on the concentration of JA-Me applied.

Indeed, gibberellic acid, as well as bromoethane, are used commercially to break dormancy and to stimulate sprout formation.

Treatments were carried out on microtubers (200–400 mg) that had been cold-stored for 8 wk to determine their effect on breaking dormancy. Signal solution was used at full strength (100%) or diluted to 20% (as for soybean), 12%, or 6% of full strength. $GA_3$ (500 mg l⁻¹), water soaking, and control treatments were performed for comparison purposes. Microtuber soaking treatments lasted 24 h and then incubation occurred either in the light (40 μmol m⁻²s⁻¹ cool-white fluorescent) or in the dark. Five microtubers were used in each treatment. Observations for sprouted microtubers were made at 1 and 2 wk.

One hundred % signal solution was as effective as $GA_3$ (500 mg l⁻¹) when evaluated after 1 wk with respect to the number of sprouted microtubers. Table 4 shows the effect of signal solution (SS) on dormancy breaking of potato microtubers as compared to the known dormancy breaker gibberellic acid ($GA_3$) (200–450 mg) that had been cold-stored at 5° C. for 8 weeks and evaluated after treatment and incubation with or without light for 1 and 2 weeks, for number of sprouts and for number with multiple sprouts (>1) at 2 weeks. One hundred % signal solution induced multiple sprouts and dark incubation favoured sprouting as compared with the light regime after 1 wk of incubation. The exact cause of dark incubation favouring 100% signal solution is not understood. One hundred % signal solution was more effective than diluted signal solution when numbers of sprouted microtubers were counted after 1 wk. After 2 wk of incubation all treatments were equally effective in causing sprouting but the signal solution and $GA_3$ solutions were most promotive of multiple sprouting which did not occur in the water soaking treatment and only in the control treatment incubated in the dark.

TABLE 4

Effects of signal solution (SS) on dormancy breaking of potato microtubers as compared to the known dormancy breaker gibberellic acid ($GA_3$)

| Treatments | Number of sprouted microtubers 1 wk | Number of sprouted microtubers 2 wk | Number of multiple sprouted microtubers (2 wk) | Mean number of sprouts ± SE |
|---|---|---|---|---|
| $GA_3$ 500 mgl⁻¹ + light | 1/5 | 5/5 | 2/5 | 2.5 ± 0.5 |
| $GA_3$ 500 mgl⁻¹ – light | 5/5 | 5/5 | 4/5 | 2.5 ± 0.3 |
| 100% SS + light | 0/5 | 5/5 | 2/5 | 2.5 ± 0.5 |
| 100% SS – light | 5/5 | 5/5 | 3/5 | 2.3 ± 0.3 |
| 20% SS + light | 0/5 | 4/5 | 0 | 0 |
| 20% SS – light | 2/5 | 5/5 | 2/5 | 2.0 ± 0 |
| 12% SS + light | 0/5 | 4/5 | 1/4 | 2.0 ± 0 |
| 12% SS – light | 2/5 | 5/5 | 2/5 | 2.0 ± 0 |
| 6% SS + light | 0/5 | 4/5 | 2/4 | 2.0 ± 0 |
| 6% SS – light | 1/5 | 5/5 | 2/5 | 2.0 ± 0 |
| Water + light | 0/5 | 4/5 | 0 | 0 |
| Water – light | 2/5 | 5/5 | 0 | 0 |
| Control + light | 0/5 | 5/5 | 0 | 0 |
| Control – tight | 1/5 | 5/5 | 1/5 | 2.0 ± 0 |

Tuber sprouting of potatoes is somewhat comparable to seed germination in the sense that the plant meristems are activated and the plant is beginning to grow, following quiescence. A signal molecule involved in bacteria-legume signalling was shown to be effective in breaking the dormancy of a plant (potato) that is distantly related to the legumes. LCOs therefore seem to have a broad effect on breaking the dormancy or quiescence of plants.

EXAMPLE 7

Effects of Combinations of $GA_3$ and 100% Signal Solution in Breaking Dormancy of Potato Tubers The data presented in Example 6 suggested that the 100% signal solution (and thus the LCO purified from *B. japonicum*) was effective in breaking microtuber dormancy. However, the microtubers used in the trial had been cold-stored for 8 wk. In this trial, the effects of signal solution were evaluated in combination with $GA_3$ on minitubers with only 3 wk of cold storage. It was also investigated whether the effect of 100% signal solution might be synergistic if used with $GA_3$ (500 mg $l^{-1}$).

Minitubers (20–30 g) with 3 wk cold storage treatment were soaked for 24 h in 500 mg $l^{-1}$ $GA_3$, 100% signal solution, or a mixture of the two. Another treatment involved successive soaking for 12 h each, in first $GA_3$, and then signal solution. A control treatment without soaking was also performed. Eight minitubers were used per treatment which were applied at room temperature (20° C.). Microtubers were observed after 2 wk and the number of sprouted minitubers and the number with multiple sprouts were counted.

All treatments were able to break minituber dormancy except the control (Table 5). The 500 mg 11 $GA_3$ treatment alone or together with 100% signal solution, for 24 h, caused 100% sprouting, and significantly more multiple sprout formation than the other treatments. The 100% signal solution alone or in combination with 500 $mg^{-1}$ $GA_3$ were as effective as 500 $mgl^{-1}$ $GA_3$ alone for breaking dormancy within 2 wk. However, less multiple sprouting occurred with 100% signal solution alone, or following 12 h $GA_3$ treatment, compared with the $GA_3$ treatment alone or the combined $GA_3$ and Signal treatments. When working under the conditions tested, there were no clear synergistic effects of 100% signal solution in combinations with 500 mg $l^{-1}$ $GA_3$ on the number of sprouted tubers or multiple sprouts.

TABLE 5

Individual and combined effects of $GA_3$ and 100% signal solution (SS) on dormancy breaking of minitubers that had been cold-stored for 3 weeks

| Treatments | Number of sprouted minituber | Number of minituber with multiple sprouts | Mean number of sprouts ± SE |
| --- | --- | --- | --- |
| $GA_3$ 500 $mgl^{-1}$ 24 h | 8/8 | 6/8 | 3.37 ± 0.62 |
| 100% SS 24 h | 7/8 | 2/7 | 1.33 ± 0.42 |
| $GA_3$ 500 $mgl^{-1}$ + 100% SS 12 h + 12 h | 8/8 | 6/8 | 2.37 ± 0.41 |
| $GA_3$ 500 $mgl^{-1}$ + 100% SS Combination 24 h | 8/8 | 6/8 | 3.75 ± 0.67 |
| Control | 0/8 | 0/8 | 0/8 |

These results suggest that bacteria-legume signal molecules are effective in breaking the dormancy of potatoes. Taken together with the results presented above (i.e. Example 4 and Table 1) showing the effects of a pure LCO in breaking the quiescence of seeds and promoting growth of a variety of distantly related plants, strongly supports the contention that LCOs are effective at breaking the dormancy of potatoes and promoting the activity of plant meristems in general.

EXAMPLE 8

Effectiveness of $GA_3$ and Signal Solution, as Compared to Bromoethane and Mechanical Injuries, in Breaking Dormancy Bromoethane (BE) was reported to break potato tuber dormancy when applied as a fumigant and it was found that BE at a concentration of 0.2 ml $l^{-1}$ was the most effective (Coleman, 1983). Conventionally, large potato tubers are cut into small pieces, each containing an eye, to be used as seed pieces. To obtain quick and uniform sprout emergence, potato tubers should be cut at least 2 wk before planting (Slomnicki and Rylski, 1964). Mechanical injury is also shown to contribute to sprout induction. The objective of this experiment was to compare the effects of known dormancy-breaking treatments on microtubers and minitubers 1) BE; 2) $GA_3$; and 3) mechanical injury; with the newly identified dormancy breaker: LCOs.

Microtubers (200–500 mg) cold-stored for 8 wk and minitubers (20–35 g) cold-stored for 0, 2, or 8 wk were used for these experiments. BE (0.2 ml $l^{-1}$) and mechanical injury (cutting in half, microwaving at full power for 10 sec) were compared with $GA_3$ (500 $mgl^{-1}$), 100% signal solution, water soaking, and control treatments. Six microtubers or minitubers were used per treatment. Observations were made at 1, 2, 3, and 4 wk intervals and the number of sprouted tubers were counted. The evaluation period was extended because tubers with little or no cold storage treatment took longer to sprout.

$GA_3$ was the only agent which was able to break dormancy of minitubers that had not been cold-stored; 0/6 at 2 wk but 4/6 by 4 wk (minituber, 0 wk storage; Table 6). Minitubers with 2 wk cold storage that were treated with $GA_3$ also broke-dormancy; 0/6 at 2 wk but 5/6 by 4 wk with 216 showing multiple shoots. Signal solution treatment of minitubers cold-stored for 2 wk caused 1/6 (with multiple shoots) minitubers to break dormancy after 4 wk. For minitubers cold-stored for 8 wk, all treatments (including water soaking and control), except the microwaving, showed some sprouting the first week and multiple sprouting was evident in the $GA_3$ (6/6), 100% signal solution (4/6), and BE (1/6) treatments by 2 wk. Cutting caused sprouting in 9/12 cut halves by 2 wk but only a few multiple shoots (2/12) were evident by 3 wk.

TABLE 6

Sprouting and (multiple sprouting) performance on minitubers and microtubers cold-stored for 0, 2, 4, or 8 weeks after exposure to Bromoethane (0.2 ml $l^{-1}$), mechanical injury (cutting in half or microwaving), $GA_3$ (500 mg $l^{-1}$), 100% signal solution, water soaking, and control treatments.

| Treatments | Minituber (CS8W) | | | | Minituber (CS2W) | | | | Minituber (NCS) | | | | Microtuber (CS8W) | | | |
|---|---|---|---|---|---|---|---|---|---|---|---|---|---|---|---|---|
| | 1 wk | 2 wk | 3 wk | 4 wk | 1 wk | 2 wk | 3 wk | 4 wk | 1 wk | 2 wk | 3 wk | 4 wk | 1 wk | 2 wk | 3 wk | 4 wk |
| $GA_3$ 500 mg $l^{-1}$ | 5/6 | 6/6 (6) | 6/6 (6) | 6/6 (6) | 0 | 0 | 3/6 | 5/6 (2) | 0 | 0 | 3/6 | 4/6 | 4/6 | 5/6 (3) | 6/6 (3) | 6/6 (6) |
| 100% Signal solution | 4/6 | 6/6 (4) | 6/6 (4) | 6/6 (4) | 0 | 0 | 0 | 1/6 (1) | 0 | 0 | 0 | 0 | 1/6 | 2/6 | 4/6/ | 6/6 (1) |
| Bromoethane 0.2 ml $l^{-1}$ | 3/6 | 4/6 (1) | 6/6 (4) | 6/6 (4) | 0 | 0 | 0 | 2/6 | 0 | 0 | 0 | 0 | 2/6 | 4/6 | 4/6 | 6/6 |
| Cutting into halves | 7/12 | 9/12 | 12/12 (2) | 12/12 (2) | 0 | 0 | 0 | 1/12 | 0 | 0 | 0 | 0 | 5/12 | 8/12 | 9/12 | 10/12 |
| Microwaving | 0 | 0 | 1/6 | 2/6 | 0 | 0 | 0 | 0 | 0 | 0 | 0 | 0 | 0 | 0 | 0 | 1/6 |
| Water | 4/6 | 5/6 | 6/6 (1) | 6/6 (1) | 0 | 0 | 0 | 0 | 0 | 0 | 0 | 0 | 2/6 | 4/6 | 6/6 | 6/6 |
| Control | 2/6 | 4/6 | 6/6 | 6/6 | 0 | 0 | 0 | 0 | 0 | 0 | 0 | 0 | 3/6 | 4/6 | 6/6 | 6/6 |

'CS' stands for cold storage;
'W' for week;
N for no
'( )' denotes number of tubers with multiple sprouts With microtubers cold-stored for 8 wk, dormancy-breaking occurred within the first week in all treatments except microwaving. After 2 wk, sprouting had progressed in all treatments; water (4/6) was similar to $GA_3$ solution (5/6), BE (4/6), signal solution (416), and cutting (8/12). Only $GA_3$ solution (3/6 at 2 wk, 6/6 at 4 wk) and signal solution (1/6 at 4 wk) caused multiple sprout formation.

Signal solution (100%) was effective in causing sprouting in minitubers with 2 or 8 wk cold storage and microtubers with 8 wk cold storage but it was ineffective on minitubers that had not been cold-stored. $GA_3$ and 100% signal solution induced multiple sprouts from different eye-points unlike the control BE, or cutting treatments, that induced single sprouts only from the rose end. BE worked well in inducing single sprouts in minitubers and microtubers with 8 wk cold-storage but was not as effective as $GA_3$ for minitubers that had not been cold-stored.

Cutting minitubers or microtubers in half after 8 wk cold storage induced single sprouts on each cut half. This occurred quite efficiently in minitubers (9/12 in 2 wk, 12/12 in 4 wk) and somewhat less efficiently with microtubers (8/12 in 2 wk, 10/12 in 4 wk). Cutting was not effective in breaking dormancy in minituber without cold storage and worked poorly in minitubers that had been cold stored for only 2 wk (0/12 after 2 wk, 1/12 after 4 wk). Sprouting from two halves was good, in the sense that by cutting minitubers or microtubers in half, two propagules, each with one sprout were derived although a very insignificant number of minituber halves (2/12) showed multiple sprouting. However, cutting was risky in that this sometimes provided opportunities for fungal or bacterial infection. Microwaving induced limited sprouting but only in minitubers or microtubers that had been cold-stored for 8 wk, and not in the minitubers with 0 or 2 wk cold storage. Microwaving caused some tuber damage that may account for the reduced sprouting observed.

In short, signal solution was effective in promoting both sprouting and multiple sprouting of mini- and micro-tubers and, of the tested treatments, only $GA_3$ was better.

EXAMPLE 9

Effectiveness of Anti-ABA Compared with Other Dormancy Breaking Treatments

Anti-Abscisic acid (anti-ABA), the acetylenic analog of ABA, has never been used to induce sprouting in dormant potato tubers since it was first shown to be an ABA antagonist (Wilen et al., 1993). However, anti-ABA has been used to terminate dormancy in canola seeds (PBI Bulletin, 1995). The objective of this experiment was to test anti-ABA for breaking dormancy in potato minitubers and compare its efficacy with other dormancy-breaking treatments.

Microtubers (200–600 mg) were cold-stored for 3 wk prior to the experiment. Seven microtubers were used per treatment. Treatments included 24 h soaks in anti-ABA or $GA_3$ (500 and 250 mg $l^{-1}$, respectively) applied alone or in combination, $GA_3$ (500 mg $l^{-1}$ in combination with 100% signal solution, and water. Bromoethane (0.2 ml $l^{-1}$) and control treatments were also performed. Observations were made after 2 wk in the dark at room temperature (20° C.). Data included number of sprouted microtubers and number of multiple sprouts. Means of sprout number were calculated only from microtubers that had sprouted.

Anti-ABA alone and in successive treatments or in combination with $GA_3$ was effective in breaking microtuber dormancy (Table 7). Among the different treatments using anti-ABA and $GA_3$ the greatest mean number of sprouts (1.8±0.48) occurred when microtubers were soaked in a mixed solution of 500 mg $l^{-1}$ $GA_3$ and 500 mg $l^{-1}$ anti-ABA for 24 h but it was not significantly different from the 500 mg $l^{-1}$ $GA_3$ treatment (1.71±0.28). The combined signal solution and $GA_3$ was not more effective than $GA_3$ alone and was less effective than any $GA_3$ and anti-ABA treatment in breaking dormancy.

TABLE 7

Sprouting performance on microtubers cold-stored for 3 weeks and evaluated at 2 weeks after exposure to dormancy-breaking agents.

| Treatments | No. sprouted microtubers | Mean No. sprouts ± SE |
|---|---|---|
| $GA_3$ 500 mgl$^{-1}$ 24 h | 7/7 | 1.71 ± 0.28 |
| $GA_3$ 500 mgl$^{-1}$ + 100% SS 24 h | 3/7 | 1.33 ± 0.29 |
| Anti-ABA 500 mgl$^{-1}$ 24 h | 5/7 | 1.4 ± 0.24 |
| Anti-ABA 250 mgl$^{-1}$ 24 h | 5/7 | 1.2 ± 0.20 |
| $GA_3$ 500 mgl$^{-1}$ 12 h + Anti-ABA 500 mgl$^{-1}$ 12 h | 6/7 | 1.33 ± 0.21 |
| $GA_3$ 250 mgl$^{-1}$ 12 h + Anti-ABA 250 mgl$^{-1}$ 12 h | 7/7 | 1.57 ± 0.29 |
| $GA_3$ 500 mgl$^{-1}$ + Anti-ABA 500 mgl$^{-1}$ Combination 24 h | 5/7 | 1.8 ± 0.48 |
| $GA_3$ 250 mgl$^{-1}$ + Anti-ABA 250 mgl$^{-1}$ Combination 24 h | 5/7 | 1.6 ± 0.24 |
| Bromoethane | 1/7 | 1.0 ± 0 |
| Water | 1/7 | 1.0 ± 0 |
| Control (no treatment) | 0/7 | 0 |

The overall results with anti-ABA underline its importance as a potential dormancy-releasing agent, as much so as $GA_3$ Anti-ABA and $GA_3$ both induced multiple sprouts but sprouts were longer after $GA_3$ than anti-ABA treatment. Both agents caused sprouts to emerge at various eyes over the tuber surface. However, the $GA_3$-induced multiple sprouts were profusely branched; a group of sprouts protruded from each eye, while the anti-ABA-induced sprouts were singles. The mechanism of dormancy breaking by anti-ABA and $GA_3$ therefore was similar, but $GA_3$ appeared stronger. These agents should be tested on an equimolar basis in the future.

EXAMPLE 10

Harvests from Minitubers Sprouted Using a Range of Dormancy-Breaking Treatments

There is only limited information on the relative yield performance of potato tubers that were treated with dormancy-breaking agents (Choudhury and Ghose, 1960; Slomnicki and Rylski, 1964). Yields from potato tubers that were treated with $GA_3$ at 25–100 mg l$^{-1}$ (Choudhuri and Ghose, 1960) or 5–40 mg l$^{-1}$ (Slomnicki and Rylski, 1964) were reduced compared with untreated controls. The objective of this experiment was to evaluate the effect of dormancy-breaking agents on subsequent yield in greenhouse pot trials.

Minitubers (20–35 g) that were cold-stored for 8 wk were given dormancy-releasing treatments including 24 h soaking in $GA_3$ (500 mg l$^{-1}$), 100% signal solution, or water. Other treatments included BE (0.2 m l$^{-1}$), cutting in half, and the control. All minitubers were observed at 3 wk following treatment and the number of sprouts were noted at the time of planting. Five minitubers per treatment were individually planted into 11×12 cm plastic pots in the greenhouse. The potting mixture was 2:1 peat:perlite without fertilizer added. The pots were arranged in a complete randomized design and watered equally every alternate day. Harvest occurred after 60 d and tuber yields (number and fresh weight) were recorded.

$GA_3$ caused significantly more sprouts per minituber (4.2±0.37) than the other treatments, with 100% signal solution (2.0±0.31) and BE (1.8±0.2) giving intermediate values, and water-soaking and cutting similar to the control (Table 8). The average number of tubers per plant was greatest in the $GA_3$ treatment (3.6); almost double that of other treatments that were not different from the control. Suprisingly, however, the mean fresh weight of tubers (per replicate i.e. pot basis) harvested from minitubers exposed to the 100% signal solution treatment was the greatest (34.97 g); greater than the control fresh weight and three times more than the $GA_3$ treatment. The size and shape of tubers harvested from the $GA_3$ treatment were small and more elongated than that of the control and other treatments. Yields from BE treated minitubers were significantly lower compared with controls. The cut halves each yielded almost the same as uncut controls and had similar fresh weight to control (28.41 vs 27.16). Two cut halves of each minituber together would effectively double control yield and bring the mean number of tubers into the $GA_3$ treatment range. However, cutting into halves posed a problem of infection and decomposition at the cut surfaces.

Thus, although signal solution is not as efficacious as $GA_3$ in breaking dormancy (as evaluated by the number of sprouts), it however is significantly more efficient than $GA_3$ in increasing the tuber yield. LCOs therefore appear as the best agents to promote dormancy breaking and yield increases in potato.

TABLE 8

Harvests after 60 d from minitubers that were forced to break dormancy by different methods.

| Treatments | Mean number sprouts at planting ± SE | Mean number of tubers produced per replicate | Mean fresh weight (g) |
|---|---|---|---|
| $GA_3$ | 4.2 ± 0.37 | 3.6* | 11.13 d |
| Culling into halves (½ minituber) | 1.2 ± 0.20 | 2.0 | 28.41 b |
| Bromoethane | 1.8 ± 0.20 | 2.0 | 14.01 d |
| 100% Signal soln. | 2.0 ± 0.31 | 1.8 | 34.97 a |
| Water | 1.2 ± 0.20 | 1.0 | 17.41 c |
| Control | 1.0 ± 0 | 2.0 | 27.16 b |

Numbers represented by the same letter are not significantly different at the 0.05 level.

It shall be recognized therefore that agricultural compositions comprising at least one LCO and gibberellic acid ($GA_3$ and others known in the art) could be advantageously used in accordance with the methods of the present invention to break dormancy and/or quiescence of crop plants.

EXAMPLE 11

Other LCOs

Following the methods described above, the LCO most abundantly produced by R. meliloti (Nod Rm-V(C$_{16:2}$, S)) was isolated and tested on alfalfa (Medicago sativa) seeds. Briefly, 10 seeds were placed in a disk of filter paper on a petri plate. The filter paper was wetted with 5 ml of the appropriate LCO solution. Data were taken at 12 hour intervals upon the radicle (an embryonic root). The number of seed with an emerged radicle were counted. Each treatment was repeated four times. The data presented in table 9 indicate a clear acceleration of growth. In this case no standard for HPLC calibration was available, so a relative dilution series was used. In addition, a cluster of peaks specifically induced by the specific flavone of *Rhizobium leguminosarum* (*bv phaseoli* [strain 127K105]) were collected and tested on corn (*Zea mays*), red clover (*Trifolium repens*, Fabaceae) and pea (*Pisum sativum*, Fabaceae) (Table 10). In each case, a stimulation of seed germination was observed. Of note, *Rhizobium leguminosarum* produces a large number of LCOs. A subset of these LCOs was selected from a range of the HPLC profile where the LCOs from *B. japonicum* and *R. meliloti* did not occur. Taken together, these results clearly demonstrate that the promoting effects of LCOs on plant growth disclosed herein are observable with LCOs from different bacterial strains involved in bacteria-legume signalling. Consequently, the presented data strongly suggests that LCOs in general should demonstrate the same effects on seed germination, seedling emergence, growth, dormancy breakage and the like.

TABLE 9

Effect of LCO isolated from *Rhizobium meliloti* (RCR 2011) on germination of alfalfa after 24 h of treatment

| Treatment | Percent Germination |
|---|---|
| Control | 16.7 b |
| $10^{-1}$ dilution | 26.6 ab |
| $10^{-2}$ dilution | 26.6 ab |
| $10^{-3}$ dilution | 36.6 a |
| LSD (p < 0.05) | 19.2 |

In column numbers followed by same letter do not differ significantly by an ANOVA protected LSD test at p < 0.05

TABLE 10

Effect of LCOs of *Rhizobium leguminosarum* bv *phaseoli* (strain 127K 105) on seed germination (%) of corn (after 48 h), red clover (after 12 h) and pea (after 48 h) at 25° C.

| Treatment | Corn | Red Clover | Pea |
|---|---|---|---|
| Control | 20 a | 43.3 bc | 26.6 b |
| $10^{-1}$ dilution | 26.6 a | 26.6 c | 26.6 b |
| $10^{-2}$ dilution | 60.0 b | 63.3 ab | 20.0 b |
| $10^{-3}$ dilution | 20.0 a | 66.6 a | 73.3 a |
| LSD (p < 0.05) | 19.9 | 23.3 | 29.7 |

In column numbers followed by same letter do not differ significantly by an ANOVA protected LSD test at p < 0.05

EXAMPLE 12

Germination Versus Emergence

Seeds of corn (cv Pioneer 3921) were surface sterilized in 2% sodium hypochlorite solution for 2 minutes and placed in 9 cm diameter Petri plates containing a sheet of filter paper soaked in 10 ml of the required test solution (LCO $10^{-5}$–$10^{-13}$). Water served as the control. Observations on germination, length of root primodia and shoot were taken after 72 h of incubation at 25° C. The data was analyzed for significance by an ANOVA protected LSD test using SAS system Version 6.1 (SAS Inc., Cary, N.C., USA).

TABLE 11

Effect of lipo chitooligosaccharide [Bj Nod-V ($C_{18:1}$ MeFuc)] on germination of corn (*Zea mays* L.) after 72 h of treatment

| Treatment | Percent germination | Length of root primodia (mm) | Length of shoot primodia (mm) |
|---|---|---|---|
| Control | 46.6 a | 32.3 a | 4.6 a |
| LCO $10^{-5}$ M | 80 bc | 53.0 ab | 12.3 ab |
| LCO $10^{-7}$ M | 73.3 b | 57.6 bc | 15.0 ab |
| LCO $10^{-9}$ M | 73.3 b | 48.0 ab | 9.6 a |
| LCO $10^{-11}$ M | 100 c | 78.6 c | 21.0 b |
| LCO $10^{-13}$ M | 80 bc | 43.0 bc | 8.3 a |
| LSD (p < 0.05) | 22.6 | 24.3 | 11.0 |

In column numbers followed by same letter do not differ significantly by an ANOVA protected LSD test at p < 0.05.

Table 11 shows that incubation of corn seeds with LCO solution significantly improved the germination of corn and increased the length of both shoot and roots.

EXAMPLE 13

Seedling Emergence-Promoting Effects of LCOs Under Field Conditions

Seeds of corn, cotton, beet, and soybean which showed promising results under laboratory conditions were tested for seedling emergence under field condition. Seeds were surface sterilized with 2% sodium hypochlorite and soaked in different concentrations ($10^{-5}$, $10^{-7}$, $10^{-9}$M) of LCO solution for 12 h. Water served as the control. The study was conducted at the experimental field of the Macdonald campus of McGill University, Ste-Anne-de-Belleveue. Quebec, Canada. The field was ploughed to a fine tilth, seeds were hand planted in 1 m rows at 2.5 to 3 cm deep with three replications per treatment. The percent seedling emergence was observed at six days after planting during which time at least 50% of the seeds emerged in the treatments. The data was analyzed for significance by an ANOVA protected LSD test using SAS system Version 6.1 (SAS Inc., Cary, N.C., USA).

TABLE 12

Effect of lipo chitooligosaccharide [Bj Nod-V ($C_{18:1}$ MeFuc)] on seedling emergence under field condition

| Treatment | Corn | Cotton | Beet | Soybean |
|---|---|---|---|---|
| Control | 41.6 a | 6.6 a | 26.6 a | 16.6 a |
| LCO $10^{-5}$ M | 80.0 b | 16.6 a | 28.3 a | 26.6 ab |
| ICO $10^{-7}$ M | 60.0 b | 60.0 b | 46.6 c | 33.3 b |
| LCO $10^{-9}$ M | 53.3 b | 23.3 a | 38.3 ab | 63.3 c |
| LSD (P < 0.05) | 35.7 | 28.0 | 16.3 | 16.6 |

In column numbers followed by same letter do not differ significantly by an ANOVA protected LSD test at p < 0.05

Table 12 shows that LCO [Bj Nod-V ($C_{18:1}$ MeFuc)] treatment enhanced the seedling emergence under field conditions of all the crop species studied. The best effect was observed in cotton where LCO at $10^{-7}$M improved ±5 the emergence by more than 9 times as compared to the control. The effective concentration of LCO varied with the species.

Table 12 also validates the laboratory results presented herein by demonstrating that the stimulatory effects of LCOs are operating on four different crops under field conditions.

Thus the present invention provides agricultural compositions and methods by which LCO could be used to enhance the germination, seedling emergence, root growth and improve early growth of crops under laboratory or field conditions.

CONCLUSION

The present invention therefore provides evidence that, among other things: (1) lipo chitooligosaccharide (LCO) treatment enhances the seedling emergence of higher plant seeds (egs. *Z. mays, L. sativa, B. vulgaris, P. vulgaris, G. max, C. sativus, B. napus* and *M. sativa*); (2) lipo chitooligosaccharide breaks the dormancy of potato (*Solanum tuberosum*) minitubers and increases their yield; (3) lipo chitooligosaccharide improves emergence and early growth, including root growth, of *Z. mays* giving a competitive advantage over non treated ones; (4) lipo chitooligosaccharide enhances the translocation of stored seed reserve; and (5) lipo chitooligosaccharide enhances seed germination.

Although the present invention has been described hereinabove by way of preferred embodiments thereof, it can be modified, without departing from the spirit and nature of the subject invention as defined in the appended claims.

REFERENCES

Dakora et al., 1996, Physiol & Molec Path 49: 1–20.
De Jong et al., 1993, Plant Cell 5: 615–620.
De Jong et al., 1997, Phytopath 87: 588–593.
Denarie et al., 1996, Annu Rev Biochem 65: 503–535.
Durrant et al., 1991, *J. Plant Growth Reg.* 1: 45–55.
Fry et al., 1993, Plant Phys 103: 1–5.
Gillette et al., 1996, J Bact 178: 2757–2766.
Heidstra et al., 1996, New Phytol 133: 25–43.
Kepczynski et al., 1992, *J. Plant Growth Reg.* 14: 211–216.
Long, 1996, Plant Cell 8: 1885–1898.
Long SR, 1989, Cell 56: 203–214.
Nap et al., 1990, Science 250: 948–954.
Pavlova et al., 1992, Plant Sci 85: 131–134.
Peters et al., 1986, Science 233: 977–980.
Peters et al., 1990, Mol. Plant-Microbe Interact. 3: 4–8.
Röhrig et al., 1995, Science 269: 841–843.
Spaink HP, 1995, Annu Rev Phytopath 33: 345–368.
Stacey et al., 1995, Soil Biol Biochem 27: 473–483.
Stacey G, 1995, FEMS Microbiol Lett 127: 1–9.
Stokkermans et al., 1995, Plant Physiol 108: 1587–1595.
Truchet et al., 1991, Nature 351: 670–673.
Verma DPS, 1992, Plant Cell 4: 373–382.
Zhang et al., 1995, Plant Physiol 108: 961–968.
Zhang et al., 1997, Soil Biol Biochem 28: 1579–1583.

What is claimed is:

1. A method for enhancing seed germination or seedling emergence of a plant crop comprising the steps of:
   providing a composition that comprises an effective amount of at least one lipo chitooligosaccharide (LCO) and an agriculturally suitable carrier; and
   applying the composition in the immediate vicinity of a seed or seedling in an effective amount for enhancing seed germination or seedling emergence in comparison to an untreated seed or seedling.

2. A method for enhancing in a non-legume, seed germination, seedling emergence or growth of a plant crop comprising the steps of:
   providing a composition that comprises an effective amount of at least one lipo chitooligosaccharide (LCO) and an agriculturally suitable carrier; and
   applying the composition in the immediate vicinity of a seed, root or plant in an effective amount for enhancing seed germination, seedling emergence or growth of said plant in comparison to an untreated plant.

3. The method according to claim 2, wherein said plant crop is selected from the group consisting of Poaceae, Cucurbitaceae, Malvaceae, Asteraceae, Chenopodiaceae, Solanaceae and Brassicaceae.

4. The method according to claim 3, wherein said plant crop is selected from the group consisting of corn, cotton, cucumber, cantaloupe, lettuce, beet, canola and potato.

5. The method according to claim 1, wherein said LCO is obtainable from a rhizobia selected from the group consisting of *Bradyrhizobium japonicum, Rhizobium meliloti* and *Rhizobium leguminosarum*.

6. The method according to claim 5, wherein said LCO is present in said composition at a concentration of between about $10^{-5}$M to about $10^{-14}$M.

7. The method according to claim 5, wherein said LCO is present in said composition at a concentration of between about $10^{-6}$M to about $10^{-12}$M.

8. The method according to claim 5, wherein said LCO is present in said composition at a concentration of between about $10^{-7}$M to about $10^{-10}$ M.

9. The method according to claim 1, wherein said composition is effective in enhancing seed germination or seedling emergence under field conditions.

10. The method according to claim 1, wherein said plant crop is a member of the Fabaceae family.

11. The method according to claim 10, wherein said plant crop is selected from the group consisting of soybean, bean, alfalfa and clover.

12. The method according to claim 10, wherein said LCO is obtainable from a rhizobia selected from the group consisting of *Bradyrhizobium japonicum, Rhizobium meliloti* and *Rhizobium leguminosarum*.

13. The method according to claim 12, wherein said LCO is present in said composition at a concentration of between about $10^{-5}$ M to about $10^{-14}$ M.

14. The method according to claim 12, wherein said LCO is present in said composition at a concentration of between about $10^{-6}$ M to about $10^{-12}$ M.

15. The method according to claim 12, wherein said LCO is present in said composition at a concentration of between about $10^{-7}$ M to about $10^{-10}$ M.

16. The method according to claim 10, wherein said composition is effective in enhancing seed germination or seedling emergence under field conditions.

17. A method for breaking the dormancy or quiescence of a plant comprising the steps of:
   providing an agricultural composition comprising at least one lipo chitooligosaccharide (LCO) and an agriculturally suitable carrier; and
   applying the composition in the immediate vicinity of a seed, tuber or root in an effective amount to enable a breaking of the dormancy or quiescence of the seed, tuber, or root, in comparison to an untreated seed, tuber, or root.

18. The method according to claim 17, wherein said plant is a member of the family of Solonaceae.

19. The method according to claim 18, wherein said plant is a potato.

20. The method according to claim 19, wherein said growth-promoting activity of said composition enables an increase in yield.

21. The method according to claim 19, wherein said composition further comprises gibberellic acid.

22. A method for enhancing seed germination or seedling emergence of a plant crop comprising the steps of:

providing a rhizobial strain that expresses a lipo chitooligosaccharide (LCO); and incubating the rhizobial strain in the immediate vicinity of one of a seed or seedling of said plant such that said LCO enhances seed germination or seedling emergence in comparison to a non-inoculated seed or seedling.

23. A method for enhancing in a non-legume, seed germination, seedling emergence or growth of a plant crop comprising the steps of:

providing a rhizobial strain that expresses a lipo chitooligosaccharide (LCO); and incubating the rhizobial strain in the immediate vicinity of one of a seed or root of said plant such that said LCO enhances seed germination, seedling emergence or growth of said plant crop, wherein said incubation enhances seed germination, seedling emergence or growth in comparison to a non-inoculated seed or root of said plant.

24. The method of claim 23, wherein said plant crop is selected from the group consisting of Poaceae, Cucurbitaceae, Malvaceae, Asteraceae, Chenopodiaceae, Solanaceae and Brassicaceae.

25. The method of claim 24, wherein said plant crop is selected from the group consisting of corn, cotton, cucumber, cantaloupe, lettuce, beet, canola and potato.

26. The method of claim 22, wherein said rhizobia is selected from *Bradyrhizobium japonicum, Rhizobium meliloti* and *Rhizobium leguminosarum.*

27. The method of claim 22, wherein said LCO enhances seed germination or seedling emergence under field conditions.

28. The method of claim 22, wherein said plant crop is a legume in the Fabaceae family and wherein said LCO enhances seed germination or seedling emergence under field conditions.

29. The method of claim 17, wherein said composition comprises a bacterial strain which expresses said LCO.

30. The method of claim 29, wherein said bacterial strain is a rhizobial strain.

31. The method of claim 1, wherein said composition comprises a bacterial strain that expresses said LCO.

32. The method of claim 31, wherein said bacterial strain is a rhizobial strain.

33. A method for enhancing seed germination or seedling emergence of a plant crop comprising the steps of:

providing a bacterial strain that expresses a lipo chitooligosaccharide (LCO); and incubating said bacterial strain in the immediate vicinity of one of a seed or seedling of said plant such that said LCO enhances seed germination or seedling emergence of said plant crop, wherein said incubation enhances seed germination or seedling emergence in comparison to a non-inoculated seed or seedling of said plant.

34. A method for enhancing seed germination or seedling emergence of a plant crop comprising the step of:

providing a bacterial strain that expresses a lipo chitooligosaccharide (LCO) in the immediate vicinity of one of a seed or seedling of said plant such that said bacterial strain, upon expression of said LCO, enhances seed germination or seedling emergence of said plant crop, in comparison to a non-treated seed or seedling of said plant.

35. The method of claim 34 wherein said bacterial strain is a rhizobial strain.

* * * * *